(12) United States Patent
Mohr

(10) Patent No.: US 8,121,793 B2
(45) Date of Patent: Feb. 21, 2012

(54) METHOD AND DEVICE FOR COMPARATIVE DISPLAY OF BIOLOGICAL DATA

(75) Inventor: Guenther Mohr, Hamburg (DE)

(73) Assignee: Eppendorf AG (DE)

( * ) Notice: Subject to any disclaimer, the term of this patent is extended or adjusted under 35 U.S.C. 154(b) by 1279 days.

(21) Appl. No.: 11/145,557

(22) Filed: Jun. 3, 2005

(65) Prior Publication Data

US 2006/0276971 A1    Dec. 7, 2006

(51) Int. Cl.
*G01N 33/48* (2006.01)
*G01N 31/00* (2006.01)

(52) U.S. Cl. ............................................ 702/19; 702/20

(58) Field of Classification Search .................. None
See application file for complete search history.

(56) References Cited

U.S. PATENT DOCUMENTS

| 5,414,809 | A | * | 5/1995 | Hogan et al. | 715/765 |
| 6,420,108 | B2 | | 7/2002 | Mack et al. | |
| 2004/0267458 | A1 | * | 12/2004 | Judson et al. | 702/20 |

* cited by examiner

*Primary Examiner* — Eric S Dejong

(74) *Attorney, Agent, or Firm* — Knobbe Martens Olson & Bear LLP

(57) ABSTRACT

Embodiments of computer systems for visualizing information and data from samples, such as nucleic acids, proteins, or other bio-polymers, are disclosed. One embodiment of a method comprises displaying first and second display areas on a display, displaying an axis dividing the first display area into first and second sub-areas, and displaying first and second axes, wherein the axes are substantially perpendicular to each other. The method further comprises displaying a plurality of bar graphs in the first display area, wherein a length of each bar graph in the first sub-area corresponds to the scalar data information of a first biological sample, and a length of each bar graph in the second sub-area corresponds to the scalar data information of a second biological sample; displaying, in the second display area, a plurality of markers, wherein each marker is related to one of the bar graphs.

18 Claims, 4 Drawing Sheets

METHOD AND DEVICE FOR COMPARATIVE DISPLAY OF BIOLOGICAL DATA

FIELD OF THE INVENTION

The present invention relates to the field of computer systems for visualizing information and data from samples. The samples may include nucleic acids, proteins or other biopolymers.

BACKGROUND OF THE INVENTION

In biotechnology a high number of experiments is required for drug discovery, for the study of various kinds of interactions between numerous components of a biological system like cells or components of cells, or for the validation of experiments and discoveries.

High throughput approaches increase the number of experiments significantly, yielding huge data volumes to be managed, processed, analyzed and studied. In many applications, the comparison of multiple data sets or experimental data from diverse experiments is required.

In such cases and when the number of data points representing such comparisons exceeds the human capability of rapid or easy appreciation and interpretation, improved visual representation is required in order to analyze the data and their results.

A very common tool is the representation of data in graphical form. For example, there is known to represent gene expression level data in form of a so called scatter plot, wherein two datasets to be compared are embedded in one graph (as in U.S. Pat. No. 6,420,108). By this means it is possible to visually inspect the data sets for further analysis and interpretation. The analysis of data can be further enhanced by computer support. For example, the user can select a data point within the graphic by a mouse click, which then triggers a display of the underlying data in terms of its sequence, whereas the data points in question may be retrieved from a specific data base.

A scatter plot is an acceptable form of data visualization when the number of data points is reasonably limited relative to the resolution of the graphic and the resolution of the image screen. For example, the presence of 1000 data points at a screen resolution of 800×600 pixels will create visual problems to the user in cases where data points are very close to each other or even do overlap.

Also, researchers are only interested in those data points which have the lowest or the highest distance to the shared inner axis of a scatter plot. However the data points of a scatter plot cannot be sorted so as to highlight data points having e.g., lowest or highest distance to the inner axis. Furthermore there is no possibility to blend out or hide data points which are not of interest, e.g., those showing the same expression level in both of two samples, by defining certain thresholds for data points to be displayed.

Prior art technology embedded in computer systems is using data files as the source of displayed data, coding means based upon a single screen display in combination with interactive events, such as mouse clicks, mouse over event handling, triggered events such as optical feedback (change of color, increased or decreased light intensity), tactile or acoustical feedback or other means of program response to the user within the screen display.

The graphics representation as described in the prior art cannot fulfill a speedy process, does not provide for sophisticated data highlighting/sorting and setting of display threshold values, nor are multiple screens at the same time ensuring proper synchronization of data in quasi real time.

SUMMARY OF THE INVENTION

It is therefore an object of the present invention to provide methods, software tools and systems for improved graphical representation and enhanced user control over the displayed data.

According to an aspect a method of representing scalar data information collected from biological samples is provided. The method comprises displaying at least first and second display areas on a display;

displaying, in said first display area, an axis dividing said first display area into first and second sub-areas;

displaying, in said second display area, first and second axes, said axes being substantially perpendicular to each other;

displaying, in said first display area, a plurality of bar graphs, wherein a length of each bar graph in said first sub-area corresponds to said scalar data information of a first biological sample, and a length of each bar graph in said second sub-area corresponds to said scalar data information of a second biological sample;

displaying, in said second display area, a plurality of markers, wherein each marker is related to one of said bar graphs, and wherein the distance X of each marker from said first axis corresponds to said scalar data information of said first biological sample, and the distance Y of each marker from said second axis corresponds to said scalar data information of said second biological sample.

The method of the invention of a split-screen like representation of scalar biological data information enables an easy and concise overview for researchers over experiment results in which details thereof are perceived in a straightforward manner. The relevant information can be recognized easier and quicker than in prior art display methods. In the present invention two different display variants are combined to benefit from the specific advantages of both variants at the same time and on the same display, that is, the bar graph chart which is best suited to represent scalar information and the marker chart which allows to recognize specific position-related information like agglomeration of data points.

In an exemplary embodiment the method further comprises receiving an input indicating a selection of one or more of said bar graphs in said first display area;

highlighting the marker(s) in said second display area which correspond(s) to said bar graph(s).

In an exemplary embodiment the method further comprises receiving an input indicating a selection of one or more of said markers in said second display area;

highlighting the bar graph(s) in said first display area which correspond(s) to said marker(s).

Highlighting allows for easy recognition of the relations between the two display variants, i.e. recognizing the relations between respective data points in the two different display areas. Selection of points to be highlighted can be achieved by known techniques like clicking or dragging frames around the data points of interest. A selection can be made either in the bar graph area or in the marker chart area, according to the above mentioned two possibilities.

In an exemplary embodiment the method further comprises
> displaying a third display area in which additional information related to said samples is displayed.

The additional information can comprise various useful data about the experiment the displayed results belong to, like an image of a used micro-array arrangement, date information, experiment conditions and the like.

In an exemplary embodiment the method further comprises
> displaying a third display area in which additional information related to the highlighted marker(s) or bar graph(s), respectively, is displayed.

The third display area can advantageously be used specifically to display information about the data point(s) currently highlighted, like sample numbers, used agent, used gene and other sample specific data.

In an exemplary embodiment the method further comprises
> arranging said bar graphs along said axis in a sorted manner, wherein said sorting is performed according to one or a combination of the following criteria:
> length of bar graph in either said first or said second sub-area;
> difference between the length of a bar graph in said first sub-area and the length in said second sub-area.

Sorting is a very useful technique for enhancing the ability of a researcher to quickly recognize the information of interest that may otherwise not be easily recognized. The lengths are indicative of the amount of the respective scalar data information and the difference in length is indicative of the important difference in reaction of the first and second sample, respectively. As will be understood better in the further description particularly this difference is of great interest in conjunction with the reaction of samples to certain genes. Sorting may also comprise to use certain threshold values for blending out uninteresting value intervals.

In an exemplary embodiment the method further comprises
> receiving an input selecting one of said at least two display areas; and
> highlighting said selected display area.

In an exemplary embodiment highlighting said selected display area comprises one of
> enlarging said display area; and
> arranging said display area in a pre-determined position on said display.

According to a second aspect of the invention a method of representing scalar data information collected from biological samples is provided. The method comprises
> displaying at least first and second display areas on a display;
> displaying, in said first display area, an axis dividing said first display area into first and second sub-areas;
> displaying, in said second display area, first and second axes, said axes being substantially perpendicular to each other;
> displaying, in said first display area, a plurality of markers, wherein the distance of a marker from said first axis corresponds to a scalar data information of said first biological sample, and the distance of a marker from said second axis corresponds to said scalar data information of said second biological sample;
> displaying, in said first display area, a plurality of bar graphs, wherein
> each bar graph is related to one of said markers;
> a length of each bar graph corresponds to the distance of the related marker from a line defined by equal distances X to said first and Y to said second axis;
> the location of said bar graph in either said first or said second sub-area corresponds to the position of the related marker either between said line and said first axis or between said line and said second axis.

According to this aspect a method similar to the first aspect is provided, however with this embodiment an advanced data representation is possible, which does contain some more information. A further description will be given in the detailed description.

In an exemplary embodiment the method further comprises
> receiving an input indicating a selection of one or more of said bar graphs in said first display area;
> highlighting the marker(s) in said second display area which correspond(s) to said bar graph(s).

In an exemplary embodiment the method further comprises
> receiving an input indicating a selection of one or more of said markers in said second display area;
> highlighting the bar graph(s) in said first display area which correspond(s) to said marker(s).

In an exemplary embodiment the method further comprises
> displaying a third display area in which additional information related to said samples is displayed.

In an exemplary embodiment the method further comprises
> displaying a third display area in which additional information related to the highlighted marker(s) or bar graph(s), respectively, is displayed.

In an exemplary embodiment the method further comprises
> arranging said bar graphs along said axis in a sorted manner, wherein said sorting is performed according to one or a combination of the following criteria:
> length of bar graph;
> location of bar graph in either said first or said second sub-area.

The sorting here is mainly similar to the one described above; the differences and the reasons therefore should be apparent to an artisan and will become clear in the detailed description of the invention.

In an exemplary embodiment the method further comprises
> receiving an input selecting one of said at least two display areas; and
> highlighting said selected display area.

In an exemplary embodiment highlighting said selected display area comprises one of:
> enlarging said display area;
> arranging said display area in a pre-determined position on said display.

According to another aspect a computer program product comprising program code means stored on a computer readable medium for carrying out the method of the invention, when said program product is run on a computer or network device.

According to yet another aspect of the present invention a computer system for presenting scalar data information collected from biological samples, comprising:
> a display;
> a data interface for receiving scalar information;

a central processing unit CPU connected with said display
  component adapted for
  displaying at least first and second display areas on said
    display;
  displaying, in said first display area, an axis dividing said
    first display area in first and second sub-areas;
  displaying, in said second display area, first and second
    axes, said axes being substantially perpendicular to
    each other;
  displaying, in said first display area, a plurality of bar
    graphs, wherein a length of each bar graph in said first
    sub-area corresponds to a received scalar information
    of a first biological sample, and a length of each bar
    graph in said second sub-area corresponds to said
    scalar information of a second biological sample;
  displaying, in said second display area, a plurality of
    markers, wherein each marker is related to one of said
    bar graphs, and wherein the distance X of each marker
    from said first axis corresponds to said scalar data
    information of said first biological sample, and the
    distance Y of each marker from said second axis cor-
    responds to said scalar data information of said sec-
    ond biological sample.

In an exemplary embodiment the system further comprises
a data input component adapted for receiving an input
  indicating a selection of at least one of said bar graphs in
  said first display area;
and wherein said CPU is further adapted for
  highlighting the marker(s) in said second display area
    which correspond(s) to said bar graph(s).

The data input component can be, but is not restricted to, a keyboard, a mouse, a trackball, a touchpad, a touchscreen or a graphic tablet. It is also possible to use combinations of the mentioned or other suitable input devices, like mouse and keyboard.

In an exemplary embodiment the system further comprises
a data input component adapted for receiving an input
  indicating a selection of at least one of said markers in
  said second display area;
and wherein said CPU is further adapted for
  highlighting the bar graph(s) in said first display area
    which correspond(s) to said marker(s).

Highlighting can be performed by any known technique, like using another colour, modified brightness values, drawing a frame around highlighted areas and the like. The artisan should be aware also of other similar highlighting possibilities, including audible and tactile variants.

In an exemplary embodiment the CPU is further adapted for
  displaying a third display area in which additional infor-
    mation related to said scalar information is displayed.

In an exemplary embodiment the CPU is further adapted for
  displaying a third display area in which additional infor-
    mation related to the highlighted marker(s) or bar
    graph(s), respectively, is displayed.

In an exemplary embodiment the CPU is further adapted for
  arranging said bar graphs along said axis in a sorted man-
    ner, wherein said sorting is performed according to one
    or a combination of the following criteria:
  length of bar graph in either said first or said second sub-
    area;
  difference between the length of a bar graph in said first
    sub-area and the length in said second sub-area.

In an exemplary embodiment the system further comprises
a data input component adapted for receiving an input
  selecting one of said at least two display areas; and
  highlighting said selected display area.

In an exemplary embodiment highlighting said selected display area comprises one of
  enlarging said display area;
  arranging said display area in a pre-determined position on
    said display.

This enables a researcher to ease up viewing by highlighting the specific display area that is showing the relevant information in the most suitable way. Enlarging can of course be combined with the arranging, e.g., such that the highlighted display area will be located on the left side of a display, and also be displayed larger than other display areas on the display.

According to still another aspect of the present invention a computer system for presenting scalar information collected from biological samples is provided. The system comprises
  a display;
  a data interface for receiving scalar information;
  a central processing unit CPU connected with said display
    component adapted for
    displaying at least first and second display areas on a
      display;
    displaying, in said first display area, an axis dividing said
      first display area in first and second sub-areas;
    displaying, in said second display area, first and second
      axes, said axes being substantially perpendicular to
      each other;
    displaying, in said first display area, a plurality of mark-
      ers, wherein the distance of a marker from said first
      axis corresponds to a scalar data information of said
      first biological sample, and the distance of a marker
      from said second axis corresponds to said scalar data
      information of said second biological sample;
    displaying, in said first display area, a plurality of bar
      graphs, wherein
      each bar graph is related to one of said markers;
      a length of each bar graph corresponds to the distance
        of the related marker from a line defined by equal
        distances X to said first and Y to said second axis;
      the location of said bar graph in either said first or said
        second sub-area corresponds to the position of the
        related marker either between said line and said
        first axis or between said line and said second axis.

The display may comprise, but is not restricted to, a TFT monitor, a cathode ray tube, a projector or other devices.

In an exemplary embodiment the system further comprises
a data input component adapted for receiving an input
  indicating a selection of at least one of said bar graphs in
  said first display area;
and wherein said CPU is further adapted for
  highlighting the marker(s) in said second display area
    which correspond(s) to said bar graph(s).

In an exemplary embodiment the system further comprises
a data input component adapted for receiving an input
  indicating a selection of at least one of said markers in
  said second display area;
and wherein said CPU is further adapted for
  highlighting the bar graph(s) in said first display area
    which correspond(s) to said marker(s).

In an exemplary embodiment the CPU is further adapted for
  displaying a third display area in which additional infor-
    mation related to said scalar information is displayed.

In an exemplary embodiment the CPU is further adapted for
  displaying a third display area in which additional information related to the highlighted marker(s) or bar graph(s), respectively, is displayed.

In an exemplary embodiment the CPU is further adapted for
  arranging said bar graphs along said axis in a sorted manner, wherein said sorting is performed according to one or a combination of the following criteria:
  length of bar graph;
  location of bar graph in either said first or said second sub-area.

In an exemplary embodiment the system further comprises receiving an input selecting one of said at least two display areas; and
  highlighting said selected display area.

In an exemplary embodiment the system further comprises a data input component adapted for receiving an input selecting one of said at least two display areas; and
  highlighting said selected display area.

In an exemplary embodiment highlighting said selected display area comprises one of:
  enlarging said display area;
  arranging said display area in a pre-determined position on said display.

BRIEF DESCRIPTION OF THE DRAWINGS

A better understanding of the invention can be achieved by referring to the attached drawings, which are provided to show exemplary embodiments of this invention, and which shall not be understood as restricting the invention to the precise embodiments shown. In the drawings

DETAILED DESCRIPTION OF CERTAIN EMBODIMENTS OF THE INVENTION

Figure 1:
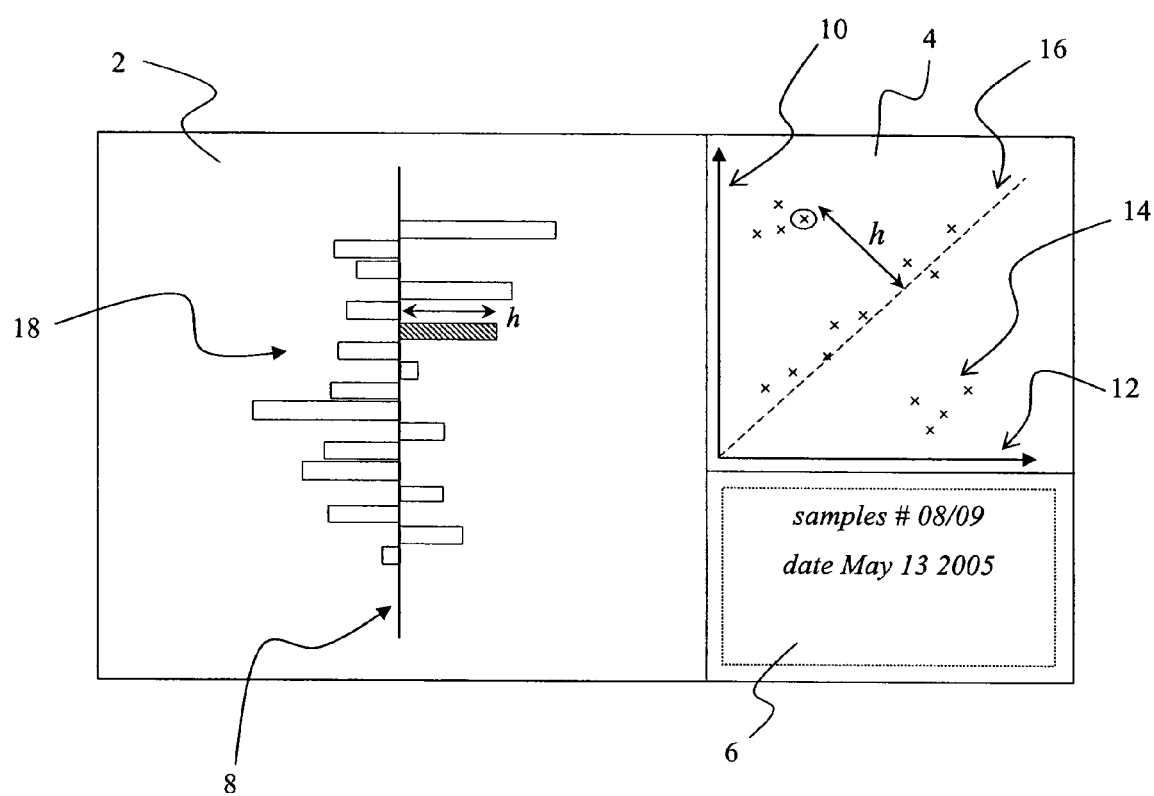
FIG. 1 shows a first embodiment of the method for displaying scalar information according to the invention.

The computer displays as used in prior art cannot take advantage of split screen data including the use of images from scan results and similar data source. Today, computers and processors allow faster execution of display algorithms. Graphic boards and displays allow faster, more color intensive and larger display formats. The combined effect results in improved work of researchers by delivering an interactive work process.

Current modern computer displays, for example 16:9 or 16:10 vs. 4:3 as demonstrated by W-XGA or the like, may have wider horizontal dimensions in relation to the vertical axis, thereby being capable to display multiple images at the same time, in a side-by-side manner. Accelerated CPUs, higher memory levels, faster graphics boards and display units, in combination with higher image resolution, can supply the user with multiple images at practically real time, also including more than two data sets at the same time in various kinds of data representation.

In light of the described better technical platforms available, an enhanced form of data representation is described below.

Embodiments of the invention assume data representations in the form of split screens, e.g., displaying more then one image at the same time. The full image screen comprises a main object/display area, which is the largest image, accompanied by other image objects at given locations as minor objects. The objects as displayed are concatenated by the computer system in such a way, when the user is working in one display area, that corresponding reaction in the other display areas is ensured as defined by the program.

More than two datasets can be displayed at the same time in one display area. The images can be swapped in such a way that a minor object can be transformed into a main object, whereas the former main object is transformed to a minor object.

The main object, i.e. the respective main display area, is highlighted either by being arranged in a pre-determined area of the display and/or by enlarging the main object in relation to the remaining objects. An examplary arrangement comprises three display areas, wherein one (the main object) is positioned on the left side of the display and occupying a comparatively large area, while two other display areas (the minor objects) are positioned on the right side of the display above one another and occupying a comparatively smaller area.

An exemplary arrangement comprises a bar graph chart, which can be sorted or remain unsorted depending on the choice of the user, displaying the distance of the data points of the scatter plot to the middle axis and their relative position (above/below middle axis), or according to other criteria, a scatter plot itself, and an image comprising the photographic representation of the array and its data, comprising its sequence and other information like statistics, data of experiment etc. As soon as a spot is selected in the main object, the focus of the concatenated image is changed in such a way, that the user receives the relevant information.

The user can advise the computer system to show data graphically or textwise by using defined user profiles, preference tables or similar. The program system uses all current art terms of event handling with regard to the selection of graphical image elements or text interfaces like text boxes, radio buttons et al for the selection of data points. The user is enabled to make notes on specific data points interactively, which may for example be added into the information display are (third display area).

The user can also be offered the capability to output the displayed data screen by display area or in total (complete screen) to a printer capable of delivering photographic output even at photo quality. The user has the option to represent data by displaying images using fixed dimensions of plot axis or by auto calibration, i.e. length and interval of the axis of the display are automatically determined by the computer system. Usually this will enable to automatically select reasonable dimensioning of the respective axis. A manual selection for problematic cases can also be offered.

The user has the option to refocus the view on specific parts by increasing or decreasing the start and end point of the displayed axis/area and the used interval (i.e. partitioning) of each axis by means of an electronic magnifying system or similar tools.

The user has the option to change the scale of a respective axis or the bar graph scale between linear, logarithmic or other suitable scales. The user can activate or deactivate the axis for x, y or an intermediate axis (defined by x=y) such as it may be the case in scatter and other plots.

FIG. 1 shows an exemplary embodiment of the present invention. Display areas 2 (main display area), 4 and 6 (minor display areas) are depicted, wherein in display area 2 a bar graph chart is displayed. A line 8 separates two sub-areas on either side of it. Bar graphs 18 are displayed, wherein the length of a respective bar graph h is indicative of a scalar information, e.g., a gene expression level or some other result value in two samples. That is, the value h is indicative of the difference in a scalar information in first and second samples, respectively. The location of a bar graph extending either to the right or the left side in this figure is related to the sign of that difference, i.e. if either a value of the scalar information is higher in the first or in the second sample. A substantially zero bar graph length is thus indicative of the situation wherein the scalar information value is substantially identical in both (first and second) samples. While the bar graph chart in this embodiment allows for quick recognition of the difference between the respective scalar information values it does not contain any information about the amounts of these values.

A second display area 4 displays another representation of the data shown in display area 2. Two axes 10 (y-axis) and 12 (x-axis) constitute a coordinate system, wherein a dashed line 16 is defined by equal distances to the axis or better equal values of the scalar information, i.e. by the equation $y=x$. A number of markers 14 is displayed in this display area 4, wherein the distances to the x- and the y-axis (or y and x values) are indicating the respective values of the scalar information in the first and the second sample. Each marker 14 is related to a bar graph 18, and vice versa, i.e. is referring to the same data point. The length h shown here is the (orthogonal) distance of a respective marker 14 to the line 16, and corresponds to the bar graph length of the related bar graph 18. The location of a marker on either side of the dashed line 16 will be reflected by the extension of the related bar graph (to left or to right).

The split-screen like way of presenting the scalar information according to this embodiment enables a quick and easy judgement by a researcher reviewing the data. On the left of this figure, i.e. in display area 2 the bar graph chart provides for easy recognition of the distance of a data point or marker 14 to the line 16, which may be the most important information for a researcher. On the other hand the right side of this figure, display area 4, there are displayed the data points or markers 14 in another mode better suited for recognizing other features (e.g., agglomeration of data points in certain areas).

While in this fashion the distance h to the middle axis 16 (which is only indicated here by an arrow for illustration purposes and will usually not be shown in an actual display according to the invention) can not be determined as quickly as in display area 2 it is easier to recognize certain groups of markers. Here there are depicted basically three such different groups, one being close to the middle axis 16, one being located between the middle axis 16 and the y-axis 10 and the last one being located between the middle axis 16 and the x-axis 12. Also shown here is that one marker 14 is highlighted (shown here be an enclosing circle, however there are also any other means possible as known in the art for highlighting), and the corresponding bar graph is highlighted by being hatched (or shown in another color etc.).

The markers 14 and the bar graphs 18 are interrelated, i.e. constituting pairs belonging to two different samples being subjected to the same experiment/conditions. The combination of the two display methods in a split-screen fashion on one common display enhances the ability of researchers to quickly gain an overview. Also shown here is a third display area 6, wherein additional information about the data shown can be displayed. Such additional information can be details about the particular experiment conducted, and/or additional information about the data points currently highlighted (there can also be highlighted more than one data point, e.g., one of the three groups shown here).

It should be noted that also even further display areas, i.e. more than three, can be provided, depending on the specific requirements. Such additional display areas could display further information about the current experiment or like. Or e.g., the information that, as previously described, can be displayed in area three can be "split": Just as an example the third display area could be used for displaying information about currently highlighted data points, i.e. contains "changing" or dynamic data, while an additional fourth area displays somehow "static" information, like basic experiment conditions or like. It should also be noted that the invention particularly concerns displaying the actual "work data", that is, the visualization of experimental data. There may also be further display areas which are used for presenting certain control options, like an open/save dialogue, user preferences settings and the like. Such commonly known elements are not part of this invention and shall not be described in detail as they are per se known to the artisan. For example the sorting of bar graphs according to this invention may be controlled using a conventional drop-down menu provided in a control bar arranged at the top section of the screen.

Figure 2:
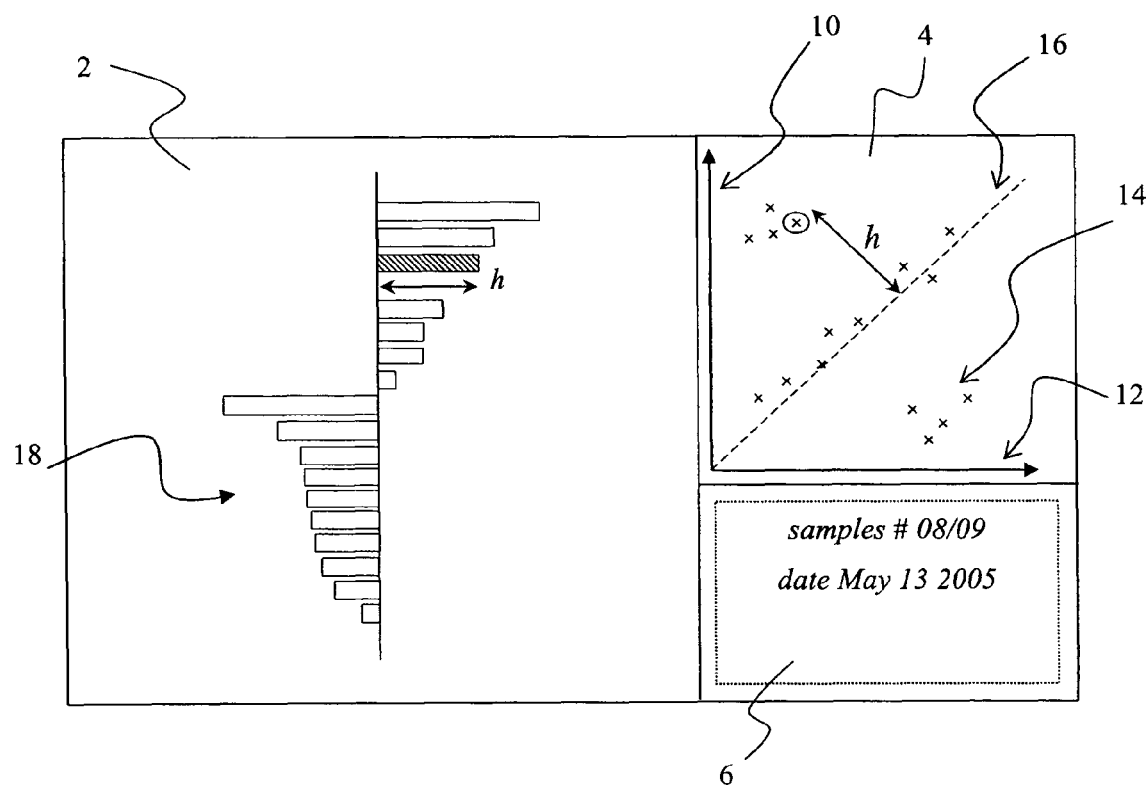
FIG. 2 shows how bar graphs can be sorted in the embodiment of FIG. 1.

FIG. 2 shows another aspect of the display method according to FIG. 1. While there is no possibility to perform some kind of sorting on the markers 14 in display area 4 the bar graphs 18 in display area 2 can easily be sorted according to different criteria, e.g., like depicted here by the length of the bar graphs in combination with the extension (left/right). That way a researcher can even more easily recognize those data points wherein the distance h is low or high. Of course the bar graphs are interrelated with the corresponding markers, according to known techniques which shall not be detailed herein, this relation being unaffected by the sorting process.

Figure 3:
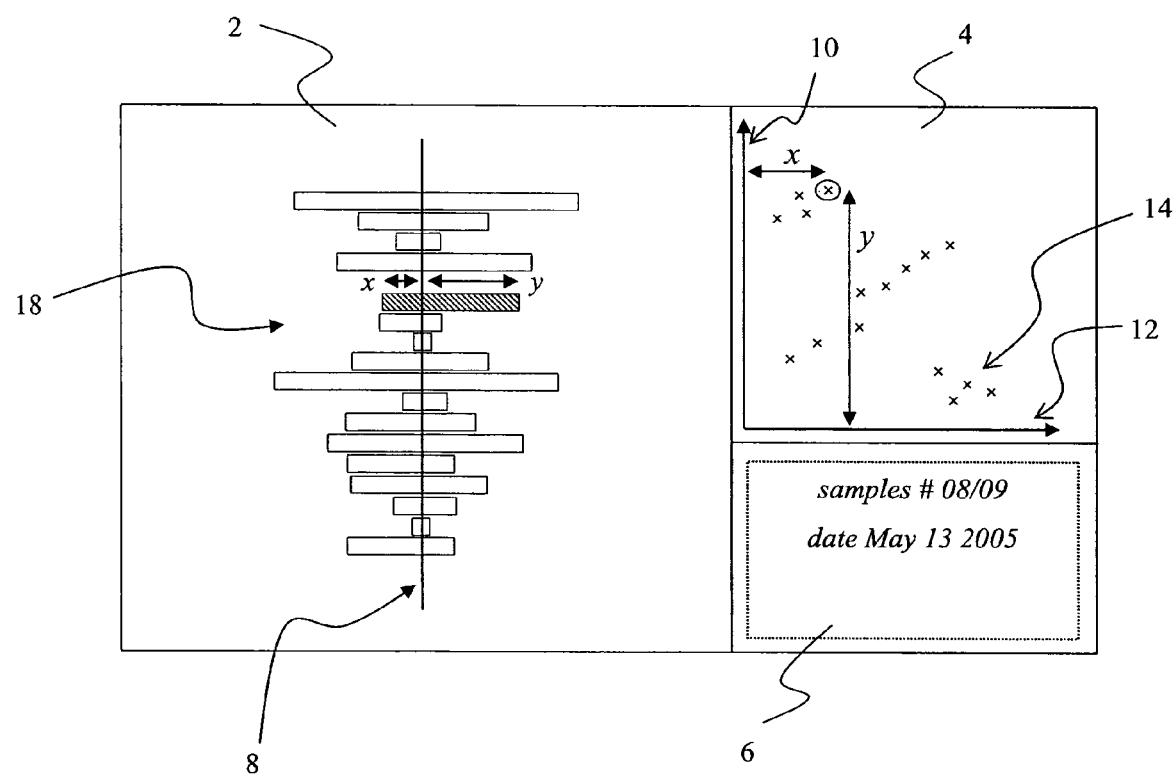
FIG. 3 shows an advanced embodiment of the method for displaying scalar information according to the invention.

FIG. 3 shows another variant of the display method of the present invention substantially similar to the ones depicted in FIGS. 1 and 2. For a detailed description of similar items shown here please refer to the description of those figures. The main difference relies in the bar graph chart on display area 2. While in FIGS. 1 and 2 only bar graphs are used that extend either to the left or the right side, bar graphs 18 as shown here can comprise contributions to both sub-areas. The extension of a particular bar graph to the left is related to the corresponding x-value of the common data point, whereas the extension of a particular bar graph to the right is related to the corresponding y-value of the common data point.

While this display variant is not as easy to oversee as those of FIGS. 1 and 2 the bar graph chart does contain some more information here. In the former only the distance h to the middle axis (omitted here) is contained in the bar graph length, while the amount of the actual x- and y-values can not be seen. However in the display variant shown here this information is still contained in the bar graph chart. While it is more complex on the one hand it does show more information on the other hand. It will depend on the specific situation which display variant provides the most suitable representation of the data.

It should be noted that the above described figures are only exemplary with respect to certain details. For example the bar graphs can also be arranged extending in another than horizontal direction, vertical or even 45° tilted extensions (the latter case corresponding closely to the middle axis 16, i.e. comprising a similar geometry) are also possible and can be advantageous depending on the specific circumstances. The actual arrangement and scaling of the different display areas is similarly only illustrative and not restricting, but may be changed according to the requirements as needed.

Not shown in these figures is another detail that is comprised within this invention, namely providing the respective data points (markers and/or bar graphs) with unique labels (e.g., samples numbers etc.) for facilitating recognition. This particularly relates to a labeling of the bar graphs, as sorting them may otherwise be confusing to the user.

Figure 4:
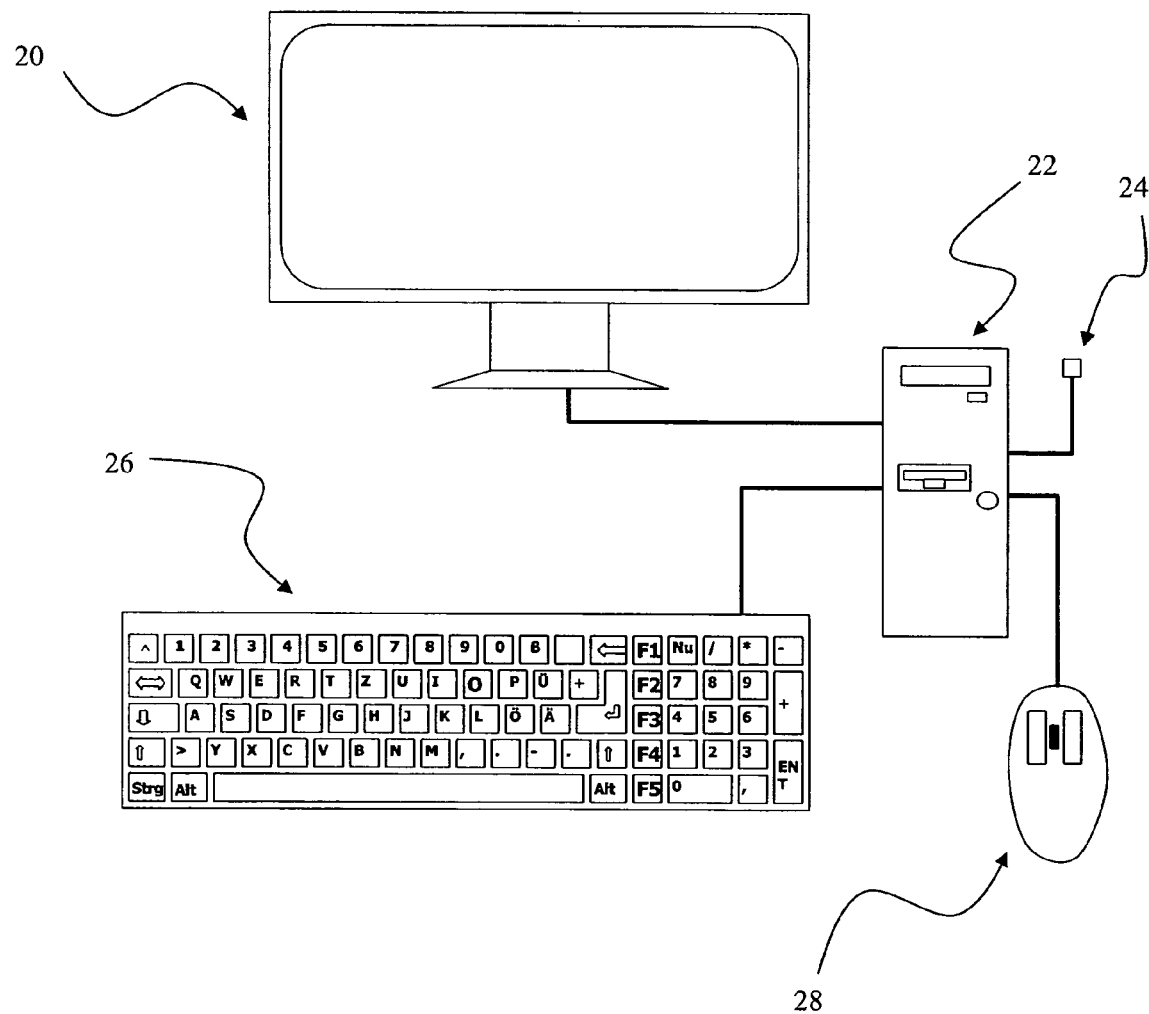
FIG. 4 shows a computer system according to the invention capable of performing the method of the invention.

FIG. 4 shows an embodiment of the computer system according to the invention for performing the method of the invention. It comprises a display 20, for example a TFT monitor or like, a central processing unit CPU 22 (symbolically depicted by a computer housing) and a data interface for receiving scalar information to be displayed. Depicted here are two input components being illustrative for all suitable input devices, a keyboard 26 and a mouse 28. The input components can be used to manipulate the displaying of the scalar information as already explained above (highlighting, selecting etc.). Other input components being within the scope of this invention may be touchscreens (i.e. the display 20 is further equipped accordingly), touchpads, graphic tablets, trackballs, and other input devices per se known in the art.

The data interface 24, though depicted here as external interface (could be any suitable wired ore wireless interface like USB, Bluetooth, WLAN or like) it may as well be implemented as internal interface. In this context the data interface 24 can also be understood as an interface to any internal memory, like CD-ROM drive, harddisk or other drives, for providing the scalar information to the CPU 22.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The scope of the invention is indicated by the appended claims rather than by the foregoing description. All changes which come within the meaning and range of equivalency of the claims are to be embraced within their scope.

The invention claimed is:

1. A method of representing scalar data comprising expression levels for a plurality of genetic loci collected from biological samples, said method comprising:
   displaying at least first and second display areas on a display;
   displaying, in said first display area, an axis dividing said first display area into first and second sub-areas;
   displaying, in said second display area, first and second axes, said axes being substantially perpendicular to each other;
   determining with a physical computer system lengths for a plurality of bar graph data depictions for said first and second sub-areas, wherein a length of each bar graph data depiction for said first sub-area represents an expression level of one of the loci of a first biological sample, and a length of each bar graph data depiction for said second sub-area represents an expression level of one of the loci of a second biological sample;
   displaying, in said first display area, the plurality of bar graph data depictions; and
   determining with the computer system locations for a plurality of marker data depictions, wherein each marker data depiction corresponds to at least one of said bar graph data depictions, and wherein the distance X of each marker data depiction from said first axis represents an expression level of one of the loci of said first biological sample, and the distance Y of each marker data depiction from said second axis represents an expression level of one of the loci of said second biological sample;
   displaying, in said second display area, the plurality of marker data depictions,
   wherein the plurality of marker data depictions and the plurality of bar graph data depictions are displayed substantially simultaneously; and
   receiving an input indicating a selection of one of the data depictions in one of the display areas, and highlighting the corresponding data depiction in the other display area.

2. The method according to claim 1, further comprising:
   receiving an input indicating a selection of one or more of said bar graph data depictions in said first display area; and
   highlighting one or more of the marker data depictions in said second display area which correspond to said one or more bar graph data depictions.

3. The method according to claim 1, further comprising:
   receiving an input indicating a selection of one or more of said marker data depictions in said second display area;
   highlighting the one or more bar graph data depictions in said first display area which correspond to said one or more marker data depictions.

4. The method according to claim 1, further comprising:
   displaying a third display area in which additional information related to said samples is displayed.

5. The method according to claim 1, further comprising:
   displaying a third display area in which additional information related to the one or more highlighted marker data depictions or bar graph data depictions, respectively, is displayed.

6. The method according to claim 1, further comprising:
   arranging said bar graph data depictions along said axis in a sorted manner, wherein said sorting is performed according to one or a combination of the following criteria:
   length of bar graph data depiction in either said first or said second sub-area;
   difference between the length of a bar graph data depiction in said first sub-area and the length in said second sub-area.

7. The method according to claim 1, further comprising:
   receiving an input selecting one of said at least two display areas; and
   highlighting said selected display area.

8. The method according to claim 7, wherein highlighting said selected display area comprises one of:
   enlarging said display area; and
   arranging said display area in a pre-determined position on said display.

9. A method of representing scalar data comprising expression levels for a plurality of genetic loci collected from biological samples, said method comprising:
   displaying at least first and second display areas on a display;
   displaying, in said first display area, an axis dividing said first display area into first and second sub-areas;
   displaying, in said second display area, first and second axes, said axes being substantially perpendicular to each other;
   determining with a computer system locations for a plurality of marker data depictions, wherein the distance of each marker data depiction from said first axis represents an expression level of one of the loci of said first biological sample, and the distance of each marker data depiction from said second axis represents an expression level of one of the loci of said second biological sample displaying, in said second display area, the plurality of marker data depictions;

determining with the computer system lengths for a plurality of bar graph data depictions, wherein:

each bar graph data depiction corresponds to one of said marker data depictions;

the length of each bar graph data depiction corresponds to the distance of the related marker data depiction from a line defined by equal distances X to said first and Y to said second axis; and the location of each bar graph data depiction in either said first or said second sub-area corresponds to the position of the related marker data depiction either between said line and said first axis or between said line and said second axis; and displaying, in said first display area, the plurality of bar graph data depictions, wherein the plurality of marker data depictions and the plurality of bar graph data depictions are displayed substantially simultaneously; and receiving an input indicating a selection of one of the data depictions in one of the display areas, and highlighting the corresponding data depiction in the other display area.

10. The method according to claim 9, further comprising:
receiving an input indicating a selection of one or more of said bar graph data depictions in said first display area;
highlighting one or more of the marker data depictions in said second display area which correspond to said bar graph data depiction(s).

11. The method according to claim 9, further comprising:
receiving an input indicating a selection of one or more of said marker data depictions in said second display area;
highlighting one or more of the bar graph data depictions in said first display area which corresponds to said marker data depiction(s).

12. The method according to claim 9, further comprising:
displaying a third display area in which additional information related to said samples is displayed.

13. The method according to claim 9, further comprising:
displaying a third display area in which additional information related to the highlighted marker data depiction(s) or bar graph data depiction(s), respectively, is displayed.

14. The method according to claim 9, further comprising:
arranging said bar graph data depictions along said axis in a sorted manner, wherein said sorting is performed according to one or a combination of the following criteria:
length of bar graph data depiction; and
location of bar graph data depiction in either said first or said second sub-area.

15. The method according to claim 9, further comprising:
receiving an input selecting one of said at least two display areas; and
highlighting said selected display area.

16. The method according to claim 15, wherein highlighting said selected display area comprises one of:
enlarging said display area;
arranging said display area in a pre-determined position on said display.

17. A non-transitory computer readable medium having a program for executing a method of representing scalar data comprising expression levels for a plurality of genetic loci collected from biological samples, said method comprising:

displaying at least first and second display areas on a display;

displaying, in said first display area, an axis dividing said first display area into first and second sub-areas;

displaying, in said second display area, first and second axes, said axes being substantially perpendicular to each other;

determining with a computer system lengths for a plurality of bar graph data depictions, wherein a length of each bar graph data depiction in said first sub-area represents an expression level of one of the loci of a first biological sample, and a length of each bar graph data depiction in said second sub-area represents an expression level of one of the loci of a second biological sample;

displaying, in said first display area, the plurality of bar graph data depictions;

determining with the computer system locations for a plurality of marker data depictions, wherein each marker data depiction corresponds to at least one of said bar graph data depictions, and wherein the distance X of each marker data depiction from said first axis represents an expression level of one of the loci of said first biological sample, and the distance Y of each marker data depiction from said second axis represents an expression level of one of the loci of said second biological sample;

displaying, in said second display area, the plurality of marker data depictions;

wherein the plurality of marker data depictions and the plurality of bar graph data depictions are displayed substantially simultaneously; and receiving an input indicating a selection of one of the data depictions in one of the display areas, and highlighting the corresponding data depiction in the other display area.

18. A non-transitory computer readable medium having a program for executing a method of representing scalar data comprising expression levels for a plurality of genetic loci collected from biological samples, said method comprising:

displaying at least first and second display areas on a display;

displaying, in said first display area, an axis dividing said first display area into first and second sub-areas;

displaying, in said second display area, first and second axes, said axes being substantially perpendicular to each other;

determining with a computer system locations for a plurality of marker data depictions, wherein the distance of each marker data depiction from said first axis represents an expression level of one of the loci of said first biological sample, and the distance of each marker data depiction from said second axis represents an expression level of one of the loci of said second biological sample;

displaying, in said second display area, the plurality of marker data depictions;

determining with the computer system lengths for a plurality of bar graph data depictions, wherein:

each bar graph data depiction is related to one of said marker data depictions;

a length of each bar graph data depiction corresponds to the distance of the related marker data depiction from a line defined by equal distances X to said first and Y to said second axis; and the location of said bar graph data depiction in either said first or said second sub-area corresponds to the position of the related marker data depiction either between said line and said first axis or between said line and said second axis;

displaying, in said first display area, the plurality of bar graph data depictions, wherein the plurality of marker data depictions and the plurality of bar graphs data depictions are displayed substantially simultaneously; and receiving an input indicating a selection of one of the data depictions in one of the display areas, and highlighting the corresponding data depiction in the other display area.

* * * * *